United States Patent [19]
Vessman et al.

[11] 3,946,063
[45] Mar. 23, 1976

[54] REAGENT FOR ELECTRONCAPTURE DETECTION AND TERTIARY AMINES

[75] Inventors: Jorgen Vessman, Skarholmen; Carl Magnus Svahn, Sollentuna; Per Hartvig, Stockholm, all of Sweden

[73] Assignee: Pierce Chemical Company, Rockford, Ill.

[22] Filed: Oct. 7, 1974

[21] Appl. No.: 512,687

[30] Foreign Application Priority Data
Mar. 28, 1974 Sweden .............................. 7404156

[52] U.S. Cl. ............ 260/463; 23/230 M; 260/471 C
[51] Int. Cl.² ......................................... C07C 69/96
[58] Field of Search ................................... 260/463

[56] References Cited
UNITED STATES PATENTS

| | | | |
|---|---|---|---|
| 3,382,207 | 5/1968 | Jaquiss | 260/463 UX |
| 3,553,214 | 1/1971 | Martin | 260/463 X |
| 3,627,799 | 12/1971 | Young et al. | 260/463 |
| 3,769,312 | 10/1973 | Gould et al. | 260/463 X |

OTHER PUBLICATIONS

Raiford, et al.; J.A.C.S., 56, pp. 1586–1590 (1934).

Takeda Chem. Ind. Ltd., C.A., 74 (1971), 53265z.

Dee, et al., C.A. 74 (1971), 12847x.

*Primary Examiner*—Joseph Paul Brust

[57] ABSTRACT

The new compound, 2,3,4,5,6-pentafluorobenzyl chloroformate, can be directly used to form amine, particularly tertiary amine, derivatives for detection by, for example, electron capture.

1 Claim, No Drawings

REAGENT FOR ELECTRONCAPTURE DETECTION AND TERTIARY AMINES

The present invention relates to new fluorinated compounds and, more particularly, to compounds of this type which can be utilized in connection with the determination of amines by analytical techniques such as electron capture.

The qualitative and quantitative determination of drugs in body fluids is an increasingly important task in bio-medical research. The development of increasingly potent drugs requires extremely sensitive methods capable of handling large numbers of samples. One of the most important techniques for this purpose is based on gas chromatography. One limiting factor is the detectability of the substances in the eluate for which a number of techniques has been developed. One of the simpler and most commonly used is based on electron capture detection. As the drugs themselves and their metabolites seldom contain electrophore groups, they usually have to be converted to derivatives giving a higher response in the detector. Highly fluorinated groups are especially suitable for this purpose.

Amines form a large and important group of physiologically active compounds, the detection of which is of great interest. As they usually give a low response in the detector, they are generally converted to derivatives before the chromatographic step. For primary and secondary amines this usually means acylation with a fluorinated carboxylic acid. A vast number of drugs consist, however, of tertiary amines, which cannot be converted simply into stable acyl derivatives. Methods have, therefore, been developed by which the tertiary amine is converted to a carbamic ester derivative of the corresponding secondary amine, hydrolysis of this carbamic ester then affording the free secondary amine which can be acylated and processed as described above. These methods, however, involve several reaction steps and are therefore laborious and, because of the number of reactions involved, losses often occur.

Accordingly, a principal object of the present invention is to provide a new reagent which can be used to convert amines to determinable derivatives.

A more particular objective resides in providing a reagent which is useful in preparing fluorinated derivatives of either primary, secondary or tertiary amines for determination by electron capture.

Another object resides in providing a fluorinated compound which can be used, in a direct reaction, to fashion a fluorinated tertiary amine.

Yet a further object is to provide a reagent for preparing fluorinated amine derivatives, wherein the derivatives can be easily prepared, are stable and have high sensitivity for analytical determination. Related thereto is the further objective of preparing amine derivatives which are susceptible to detection, by electron capture, in very small amounts.

Other objects and advantages of the present invention will become apparent as the description proceeds.

While the present invention will be described in connection with certain preferred embodiments, it is to be understood that it is not to be limited to only those embodiments disclosed. On the contrary, it is intended to cover all modifications and alternatives falling within the spirit and scope of the invention as expressed in the appended claims.

In one of its important aspects, the present invention provides new reagents for preparing fluorinated derivatives of amines. These reagents are the 2,3,4,5,6-pentafluorobenzyl haloformates and can be represented as follows:

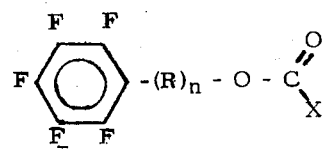

wherein: X is a halogen atom; R is alkylidene, either straight or branched chain having up to about 6 carbon atoms; and n is an integer of zero or one. Preferably, for electron capture, R is a small group such as methylene, dimethylene or 1-methyl dimethylene. As to X, Cl and Br are preferred since they readily yield reactive, stable formates. A preferred reagent is 2,3,4,5,6-pentafluorobenzyl chloroformate (X is Cl).

These new reagents can be prepared by reacting a pentafluorobenzene substituted alcohol, e.g., benzyl alcohol, or phenol with a carbonyl dihalide, e.g., phosgene. The reaction can be accomplished according to standard methods for the preparation of halo-formates from phenols. Raiford and Inman, *J. Am. Chem. Soc.*, 56, 1586 (1934). The reaction, in accordance with a further aspect of this invention is preferably accomplished in an organic solvent in the presence of an organic base such as an amine, and preferably a tertiary amine such as dimethylaniline or pyridine.

The reagents identified above are useful in applications involving the analytical determination (either qualitative or quantitative) of amines. They are particularly useful in those applications wherein the amine to be determined is derivatized to contain an electrophore group. Detection by electron capture is an example of such an analytical technique, and the present reagent is especially useful for detection of tertiary amines. However, as is recognized, the gas chromatography of amines (primary, secondary and tertiary) in trace amounts is often complicated by adsorptive losses on the column, and that these losses are reduced on derivatization. And, the novel pentafluorobenzyl carbamates have excellent properties also in this respect. Therefore, these novel reagents are also an excellent acylating agent for the derivatization of primary and especially secondary amines, as well as tertiary amines, for analytical determination of amines, in general, and particularly where such determination involves gas chromatography.

Pentafluorobenzyl amine derivatives, of either primary, secondary and tertiary amines, can be conveniently prepared in one step in the following way. The amines are extracted from an alkaline aqueous phase as bases into an organic solvent, preferably a hydrocarbon like heptane. The organic phase is separated and to this phase is some μl of the pentafluorobenzyl halo formate alkylate added. Sodium carbonate is added to catalyze the reaction. (See Hartvig and Vessman, *Analytical Letters*, 7(4), 223–231 (1974), for effect of catalyst on reaction.) The mixture is heated on a boiling water bath for 30 minutes or more if required. Then, for use, a suitable volume of the derivative is injected into the gas chromatographic column.

With the preferred reagent, the chloroformate, the reaction with a tertiary amine to afford in one step the 2,3,4,5,6-pentafluorobenzyl carbamic ester derivative of the dealkylated amine can be represented as follows:

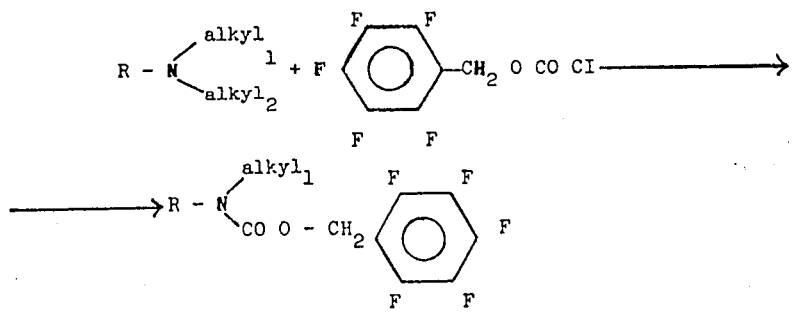

which derivative can be directly submitted to the chromatographic determination.

The following examples illustrate this invention:

EXAMPLE I

Preparation of 2,3,4,5,6-pentafluorobenzyl Chloroformate 2,3,4,5,6-pentafluorobenzyl alcohol (12.5 g, 0.063 mole) is dissolved in toluene (34.2 ml) containing 20% phosgene (0.069 mole). The solution is stirred and dimethylaniline (9.6 ml, 0.075 mole) is added during 20 minutes. The mixture is stirred for 1 h at 20° – 25° C. Water and toluene are added and after separation the toluene solution is washed with 2 N hydrochloric acid and water.

Drying over calcium chloride and concentration in vacuo below 40° C yields an oil (15.4 g) of about 85% pentafluorobenzyl chloroformate, about 5% pentafluorobenzyl alcohol and about 10% of toluene as indicated by NMR analysis. The yield of chloroformate calculated from the starting material (pentafluorobenzyl chloroformate shows a characteristic band at 1780 cm$^{-1}$ (chloroformate carbonyl) in the IR spectrum and an NMR signal at $\gamma 5.35$ (triplet, J=2Hz).

EXAMPLE II

Determination of N,N-dimethyl-(3,3-diphenyl-1-methyl propyl) amine

1. To six aqueous samples containing 12 – 120 µg of N,N-dimethyl-(3,3-diphenyl-1-methyl propyl) amine and 60 µg of the internal standard (N,N-dimethyl-(3,3-diphenyl-propyl) amine are added 0.5 ml of 1 M NaOH and 0.25 ml of heptane. The tubes are extracted for 10 minutes. After extraction the heptane phase is transferred to another centrifuge tube.

2. 50 µ of pentafluorobenzyl chloroformate and 10 mg of sodium carbonate are added, an air condenser is attached and the mixture is heated for 30 minutes on a boiling water bath.

3. The reaction mixture is shaken with 1 M NaOH and 1 – 2 µl of the organic phase is injected into a Varian 1400 gas chromatograph equipped with a flame ionization detector and a 0.9m × 1.8 mm glass column filled with 3% OV-17 on Gas Chrom P 100 – 120 mesh, acid washed and silanized. The column temperature was 210° C and the nitrogen flow 30 ml/min, giving a retention time of 5 minutes for the derivative of N,N-dimethyl-(3,3-diphenyl-1-methyl propyl) amine.

When studied in an electron capture detector with $^{63}$Ni source, these derivatives could be traced down to 3 pg.

Determination of 2-diphenyl methoxy-N,N-dimethylethyl amine can be performed in an analogous manner.

EXAMPLE III

Determination of N-methyl-(3,3-diphenyl-1-methyl propyl) amine

1. To six aqueous samples containing 5 – 130 µg of N-methyl-(3,3-diphenyl-1-methyl propyl)amine and 50µg of the internal standard N-methyl-(3,3-diphenyl-propyl) amine are added 0.5 ml of 1 M NaOH and 0.25 ml of heptane. The tubes are extracted for 10 minutes. After extraction the heptane phase is transferred to another centrifuge tube.

2. 50µl of pentafluorobenzyl chloroformate and 10 mg of sodium carbonate are added, an air condenser is attached and the mixture heated for 30 minutes on a boiling water bath.

3. Continue according to Example II. When studied in an electron capture detector, these derivatives could be traced down to 3 pg.

EXAMPLE IV

Determination of (3,3-diphenyl-1-methyl propyl) amine

1. The determination is performed in a manner analogous to that described for N-methyl-(3,3-diphenyl-1-methyl propyl) amine in Example III. When studied in an electron capture detector, these derivatives could be traced down to 50 pg.

As illustrated, the procedure for preparing amine derivatives is markedly simplified by the use of the novel reagent. It has also been found that the pentafluorobenzyl carbamic esters show other advantages as derivatives for gas chromatography, such as extremely high electron capture response and high volatility, thus permitting the use of lower column temperatures as indicated in Table 2, in which some pentafluorobenzyl carbamates (PFB) of tertiary amines (Table 1) are compared with carbamates from p nitrobenzyl-and benzyl chloroformates.

TABLE 1
Structure of the tertiary amines studied

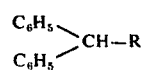

| Compound | R | Generic or Trade Name |
|---|---|---|
| 1 | —CH$_2$CH(CH$_3$)N(CH$_3$)$_2$ | Recipavrin$^{(R)}$ |
| 2 | —CH$_2$CH$_2$N(CH$_3$)$_2$ | — |
| 3 | —OCH$_2$CH$_2$N(CH$_3$)$_2$ | Diphenhydramine |

TABLE 2

Minimum Detectable Quantities (MDQ) of some Carbamates

| Derivatives | Column oven temperature °C | Retention time, min | Detector foil temperature °C | MDQ × 10$^{15}$ moles/sec |
|---|---|---|---|---|
| PFB carbamate of compound 1 | 210 | 5.8 | 190 | 0.17 |
| | | | 270 | 0.12 |
| PFB carbamate of compound 3 | 210 | 8.1 | 190 | 0.14 |
| | | | 270 | 0.11 |
| PFB carbamate of compound 2 | 210 | 6.8 | 190 | 0.14 |
| | | | 270 | 0.11 |
| Nitrobenzyl of compound 1 carbamate | 260 | 6.9 | 290 | 9.4 |
| Benzyl carbamate compound 1 | 250 | 2.2 | 290 | 670 |

While the present invention has been illustrated with respect to the detection of certain amines, it will be appreciated that the method herein disclosed is also suitable for quantitative applications and also with respect to other amines which form carbamates in the presence of the reagent, and preferably a catalyst. As discussed by Hartvig and Vessman, J. Chromatographic Sci., 12, pp. 722,724(1974), the tricyclic antidepressant imipramine and its analogues, e.g., chloroimipramine, trimipramine and amitriptyline give high yields of the carbamate. Methadone and promethazine, however, are deaminated.

As also discussed in the above article, although some side products are formed, the reaction with the new reagents can be utilized in quantitative determinations by choosing a proper internal standard. Thus, a standard curve was constructed for imipramine in the range 50 – 800μg. Chloroimipramine was used as internal standard since it reacted very similar to imipramine. The recovery at the 200μg level was 100 ± 2.7%. To fully utilize the sensitivity of the derivatives in an electron capture detector, the excess of the reagent must be removed before the gas chromatographic step.

We claim:
1. The compound 2,3,4,5,6-pentafluorobenzyl chloroformate.

* * * * *